US00PP33361P3

(12) United States Plant Patent
Buttgereit

(10) Patent No.: US PP33,361 P3
(45) Date of Patent: Aug. 17, 2021

(54) ***THUNBERGIA* PLANT NAMED 'VOLTHU 9327'**

(50) Latin Name: *Thunbergia alata*
Varietal Denomination: VOLTHU 9327

(71) Applicant: Volmary GmbH, Münster (DE)

(72) Inventor: Christian Buttgereit, Münster (DE)

(73) Assignee: Volmary GmbH, Münster (DE)

( * ) Notice: Subject to any disclaimer, the term of this patent is extended or adjusted under 35 U.S.C. 154(b) by 0 days.

(21) Appl. No.: 17/025,060

(22) Filed: Sep. 18, 2020

(65) Prior Publication Data

US 2021/0153405 P1 May 20, 2021

Related U.S. Application Data

(60) Provisional application No. 62/974,130, filed on Nov. 15, 2019.

(51) Int. Cl.
*A01H 5/02* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen M Redden
(74) *Attorney, Agent, or Firm* — The Webb Law Firm

(57) ABSTRACT

A new and distinct variety of *Thunbergia* plant that exhibits white colored petals with a dark purple colored flower tube that produces numerous flowers throughout the flowering season.

3 Drawing Sheets

Botanical classification: *Thunbergia alata.*
Varietal denomination: 'VOLTHU 9327'.

BACKGROUND OF THE INVENTION

The present invention comprises a new and distinct variety of *Thunbergia* plant, botanically known as *Thunbergia alata*, and having the varietal denomination of 'VOLTHU 9327'.

The new variety was discovered in August of 2017 in a cultivated area in Münster, Germany as a result of open pollination from proprietary breeding material (exact parentage unknown). The new variety was first asexually reproduced via cuttings in Münster, Germany in August of 2017. The new variety has been trial and field tested and has been found to retain its distinctive characteristics and remain true to type through successive propagations. The present invention has not been evaluated under all possible environmental conditions. The phenotype may vary with variations in environment without a change in the genotype of the plant.

When compared to *Thunbergia* variety named 'White Eye' (unpatented), the varieties are similar in having a white flower color, but 'VOLTHU 9327' exhibits better garden performance during the summer season, larger flowers, and more flowers per stem than 'White Eye'.

The following characteristics distinguish 'VOLTHU 9327' from other *Thunbergia* varieties known to the breeder:

Large flower number and size;
Good flowering performance during the summer season;
Well-branched; and
Rich green foliage color.

BRIEF DESCRIPTION OF THE DRAWINGS

The photographic drawings in the form of color photographs provided herein illustrate the new variety at approximately 16 weeks of age, with the colors being as nearly true as is possible with color illustrations of this type.

DETAILED BOTANICAL DESCRIPTION

Figure 1:
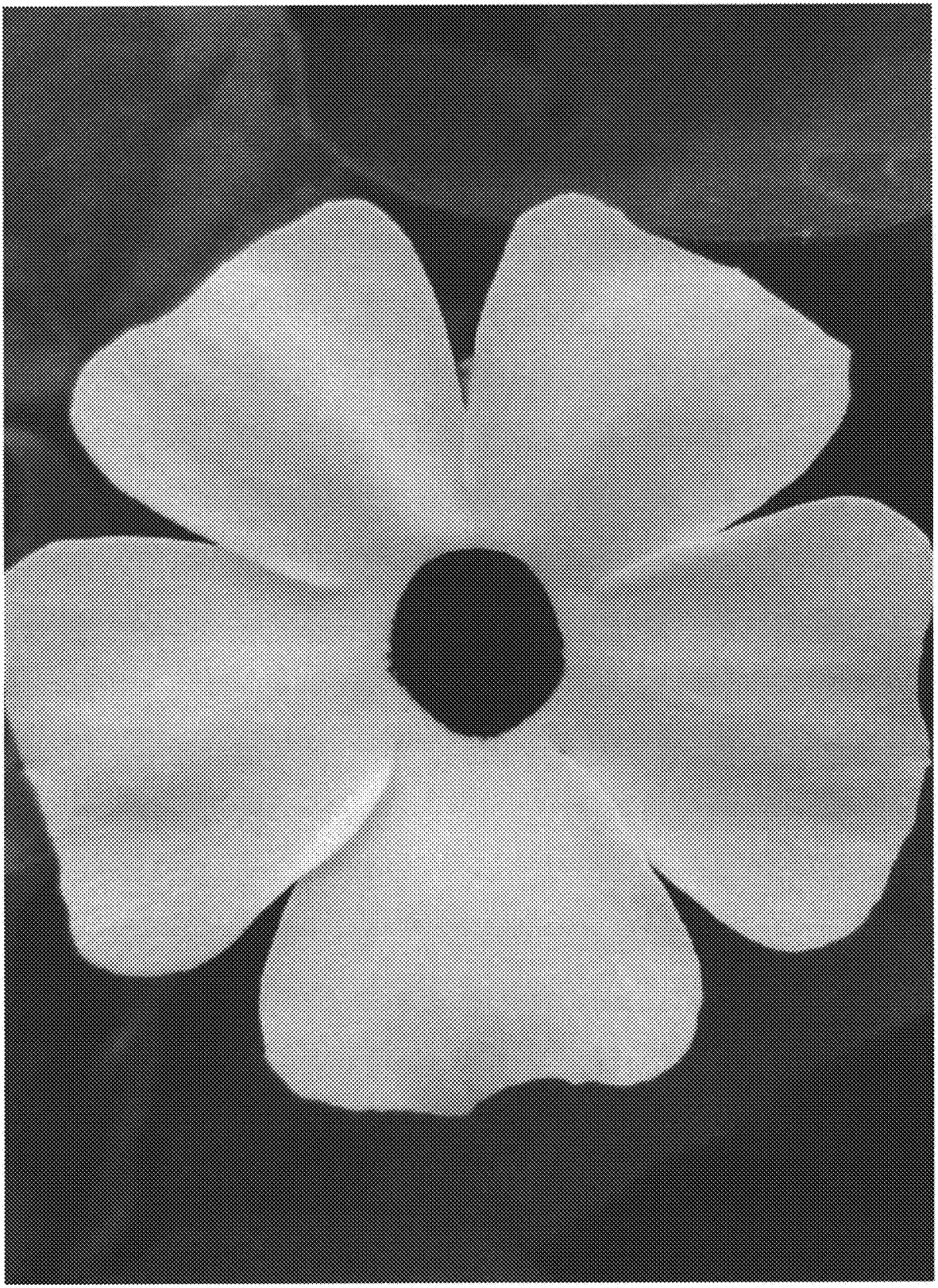
FIG. 1 is a close-up image of a flower of 'VOLTHU 9327'.
Figure 2:
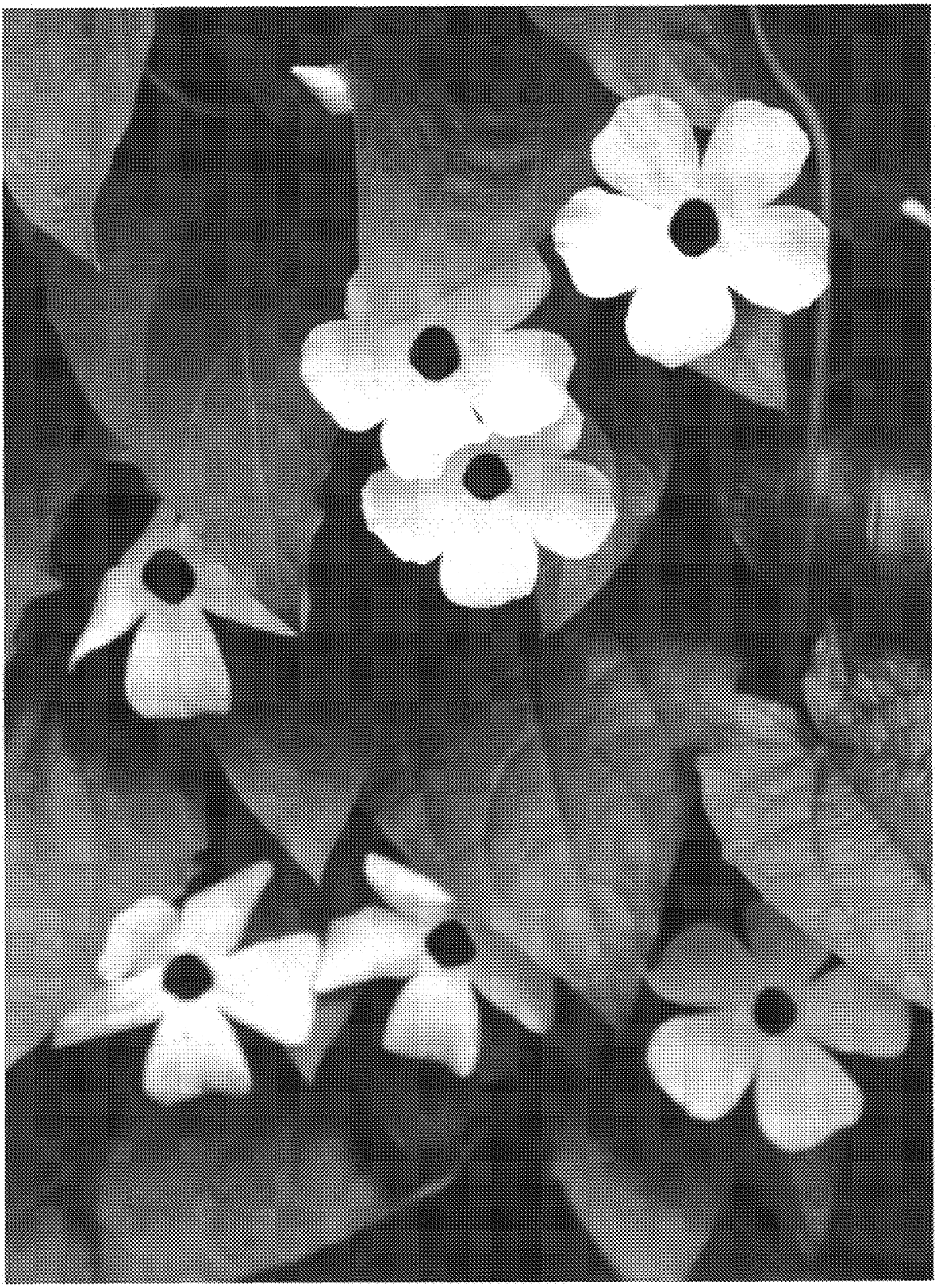
FIG. 2 is a close-up image of a flowering plant of 'VOLTHU 9327'.
Figure 3:
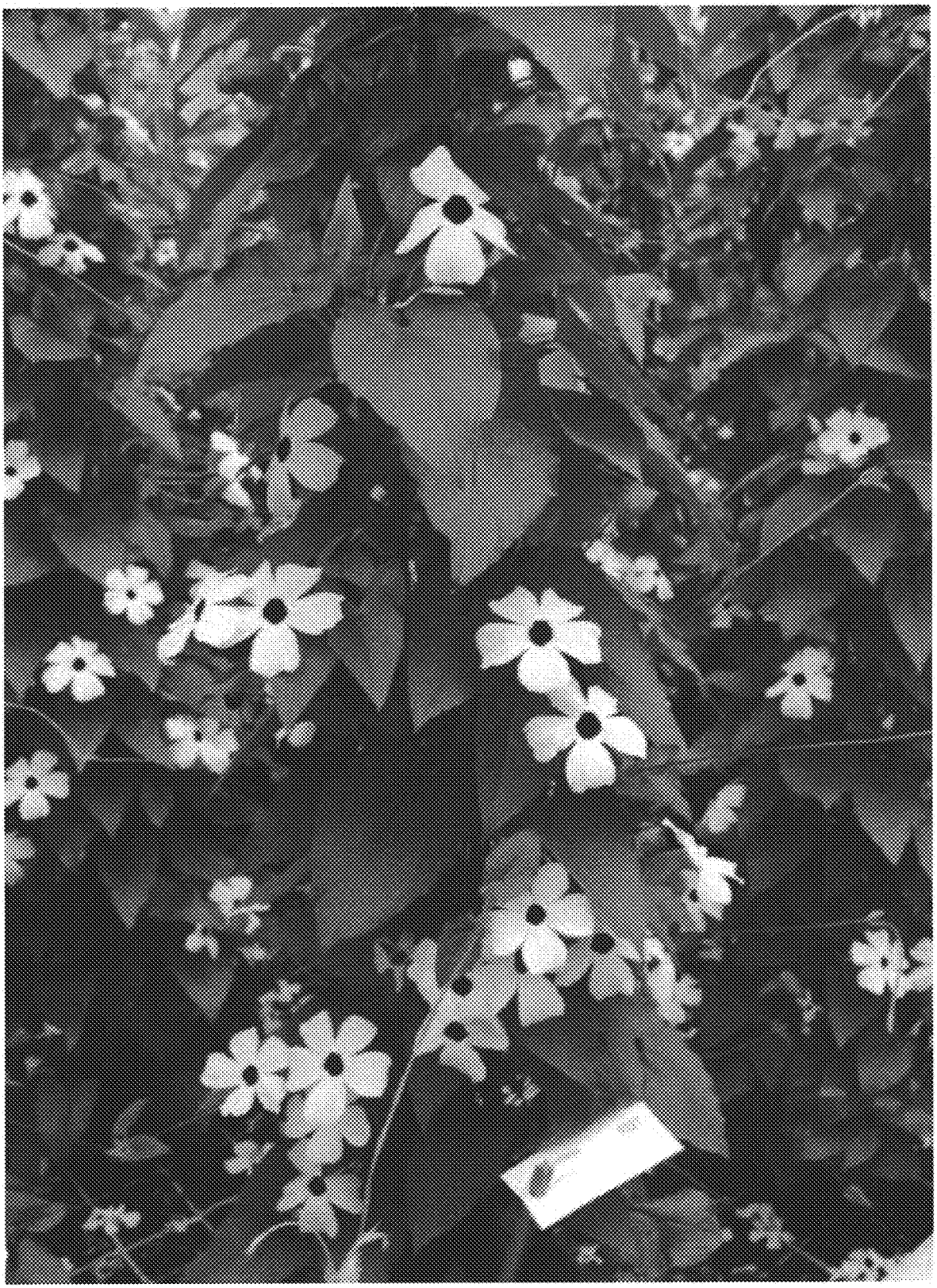
FIG. 3 illustrates flowering plants of 'VOLTHU 9327'.

The following detailed description sets forth the characteristics of the new variety. The data which defines these characteristics were collected by asexual reproductions via cuttings carried out in Münster, Germany The new variety was grown in 3 liter pots in a glass covered greenhouse during the spring in Münster, Germany with day temperatures from 18 to 20 degrees Celsius and night temperatures from 15 to 18 degrees Celsius. The light level was about 5,000 to 40,000 lux with shading started at 60,000 lux. No growth retardants were applied. The color readings were taken inside in a glass covered hall near the greenhouse under late morning daylight and the variety was approximately 16 weeks of age when described. Color references are primarily to The R.H.S. Colour Chart of The Royal Horticultural Society of London, Sixth Edition, except where terms of ordinary significance are used.

PLANT

Time to initiate roots: About 7-14 days at about 15-23° C.
Time to develop roots: About 10 days at about 15° C.
Time to produce a finished flowering plant from a rooted cutting: About 10 weeks in a 14.0 cm container.
Rooting habit: Freely branching with yellowish white, thin and fibrous roots.
Form: Climbing upward.

Height from media surface to top of foliage: Approximately 80.0-100.0 cm
Height from media surface to top of flowers: Approximately 5.0-10.0 cm.
Plant diameter: Approximately 35.0 cm.
Vigor: Medium to strong.
Disease/pest resistance: None observed to date.
Temperature tolerance: Tolerates temperatures from 5° C. to 38° C.
Drought tolerance: None observed to date.
Branching habit: Freely branching with lateral branches that potentially develop at every node.
Lateral branches:
*Length*.—80.0-100.0 cm at the time of description, but branches can reach over 2.0 m long in one growing season.
*Diameter*.—Approximately 0.2 cm.
*Internode length*.—Up to 14.0 cm.
*Texture*.—Light pubescence present.
*Color*.—RHS 142A.
Foliage:
*Arrangement*.—Opposite; simple.
*Length*.—Approximately 8.0-11.5 cm.
*Width*.—Approximately 5.7-9.0 cm.
*Shape of leaf*.—Deltoid; spear-shaped.
*Apex*.—Acute; cuspidate.
*Base*.—Concave and bow-shaped.
*Margin*.—Entire.
*Texture* (*both surfaces*).—Light pubescence present with low luster. Color: Young leaves: Upper surface: RHS 137B. Lower surface: RHS 147B. Mature leaves: Upper surface: RHS 137B. Lower surface: RHS 147B.
*Petiole*.—Length: Approximately 6.0-9.0 cm. Diameter: Approximately 2.5-9.0 mm. Texture: Light pubescence present. Color: RHS 137B.
*Veins*.—Venation type: Pinnate. Color. Upper surface: RHS 147B. Lower surface: RHS 147B.

FLOWERS

Flower arrangement: Single.
Flower habit: Trumpet-like.
Natural flowering season: Plants flower continuously from April until frost in Münster, Germany.
Fragrance: None observed.
Diameter: Approximately 6.0 cm.
Height: Approximately 2.7 cm.
Buds (described at full development):
*Length*.—Approximately 3.0 cm.
*Diameter*.—Approximately 2.0 cm.
*Shape*.—Lanceolate to deltoid.
*Color*.—RHS 145A.
Corolla:
*Petals*.—Color: Upper surface (when opening): RHS NN155A. Upper surface (fully opened): RHS NN155A. Lower surface (when opening): RHS NN155B. Lower surface (fully opened): RHS NN155B. Shape: Broadly elliptic to rounded. Length: Approximately 1.8 cm. Width: Approximately 1.6 cm. Apex: Sunked. Base: Fused. Margin: Entire, with occasional incisions. Number per whorl: 5. Texture: Smooth.
*Tube color*.—RHS N79A.
Sepals: Not applicable.
Peduncles:
*Length*.—Approximately 2.3-8.0 cm.
*Width*.—Approximately 0.1 cm.
*Texture*.—Light pubescence present.
*Color*.—RHS 145A.
*Strength*.—Strong.

REPRODUCTIVE ORGANS

Stamens:
*Number per flower*.—4.
*Anthers*.—Shape: Ovate. Length: Approximately 1.0 cm. Color: RHS NN155A.
*Pollen*.—Color: RHS NN155A. Amount: Moderate.
Pistils:
*Number per flower*.—1.
*Style*.—Length: Approximately 1.7 cm. Color: RHS NN155D.
*Stigma*.—Shape: Two-parted. Color: RHS NN155D. Size: 0.2 cm.
*Ovaries*.—Color: RHS NN155D.
Seeds:
*Number*.—1-2.
*Length*.—Approximately 0.3-0.5 cm.
*Diameter*.—Approximately 0.3-0.5 cm.
*Color*.—RHS N187A.

I claim:
1. A new and distinct variety of *Thunbergia* plant named 'VOLTHU 9327' as is herein described and illustrated.

* * * * *